US010532038B2

(12) United States Patent
Ibáñez Cabeza et al.

(10) Patent No.: US 10,532,038 B2
(45) Date of Patent: Jan. 14, 2020

(54) BETA-3 ADRENOCEPTOR AGONISTS FOR THE TREATMENT OF PULMONARY HYPERTENSION

(71) Applicants: FUNDACIÓN CENTRO NACIONAL DE INVESTIGACIONES CARDIOVASCULARES CARLOS III (CNIC), Madrid (ES); Hospital Clínic de Barcelona, Barcelona (ES)

(72) Inventors: Borja Ibáñez Cabeza, Madrid (ES); Ana García-Álvarez, Barcelona (ES); Valentín Fuster Carulla, Madrid (ES)

(73) Assignees: FUNDACÍON CENTRO NACIONAL DE INVESTIGACIONES CARDIOVASCULARES CARLOS III (CNIC), Madrid (ES); HOSPITAL CLÍNIC DE BARCELONA, Barcelona (ES)

(*) Notice: Subject to any disclaimer, the term of this patent is extended or adjusted under 35 U.S.C. 154(b) by 0 days.

(21) Appl. No.: 14/424,861

(22) PCT Filed: Aug. 28, 2013

(86) PCT No.: PCT/ES2013/070611
§ 371 (c)(1),
(2) Date: Feb. 27, 2015

(87) PCT Pub. No.: WO2014/033343
PCT Pub. Date: Mar. 6, 2014

(65) Prior Publication Data
US 2015/0374655 A1 Dec. 31, 2015

(30) Foreign Application Priority Data
Aug. 29, 2012 (ES) .................. 201231343

(51) Int. Cl.
A61K 31/426 (2006.01)
A61K 31/195 (2006.01)
A61P 9/00 (2006.01)
A61K 31/216 (2006.01)
A61K 31/36 (2006.01)
A61K 31/4412 (2006.01)
A61K 31/55 (2006.01)
A61K 31/5517 (2006.01)
A61K 31/63 (2006.01)

(52) U.S. Cl.
CPC .......... A61K 31/216 (2013.01); A61K 31/195 (2013.01); A61K 31/36 (2013.01); A61K 31/426 (2013.01); A61K 31/4412 (2013.01); A61K 31/55 (2013.01); A61K 31/5517 (2013.01); A61K 31/63 (2013.01)

(58) Field of Classification Search
CPC ............................ A61K 31/426; A61K 31/195
USPC ................................. 370/370, 567
See application file for complete search history.

(56) References Cited

FOREIGN PATENT DOCUMENTS

EP 2620143 A1 7/2013
WO WO-2011/161427 A2 12/2011

OTHER PUBLICATIONS

Definition of prevent, Princeton University "About WordNet." WordNet. Princeton University. 2010. <http://wordnet.princeton.edu>, accessed Sep. 18, 2012.*
Austin et al. Heritable Pulmonary Arterial Hypertension. Jul. 18, 2002 [Updated Jun. 11, 2015]. In: Pagon RA, Adam MP, Ardinger HH, et al., editors. GeneReviews® [Internet]. Seattle (WA): University of Washington, Seattle; 1993-2016. Available from: http://www.ncbi.nlm.nih.gov/books/NBK1485/, accessed Jul. 1, 2016.*
Takasu et al. Journal of Pharmacology and Experimental Therapeutics 2007, 321 (2), 642-647.*
Baliga et al. British Journal of Pharmacology 2011, 163, 125-140.*
Arch, J. R. S. European Journal of Pharmacology 2002, 440, 99-107.*
De Souza et al. Current Pharmaceutical Design 2001, 7, 1433-1449.*
Sawa et al. Current Medicinal Chemistry 2006, 13, 25-37.*
Rosenkranz Clin. Res. Cardiol. 2007, 96, 527-541.*
Dumas et al., "Influence of β-adrenoceptor agonists on the pulmonary circulation. Effects of a β3-adrenoceptor antagonist, SR 59230A," European Journal of Pharmacology, vol. 348, pp. 223-228, 1998.
International Search Report for PCT/ES2013/070611, dated Nov. 29, 2013.
Kozlowska et al., "Ligands at β2-, β3-, and the Low-Affinity State of β1-Adrenoceptors Block the α1-Adrenoceptor-Mediated Constriction in Human Pulmonary and Rat Mesenteric Arteries," J. Cardiovasc. Pharmacol., vol. 46, No. 1, pp. 76-82, 2005.
Tamaoki et al., "Atypical Adrenoceptor-Mediated Relaxation of Canine Pulmonary Artery through a cAMP-Dependent Pathway," Biochemical and Biophysical Research Communications, vol. 248, pp. 722-727, 1998.
Vrydag et al., "Tools to study β3-adrenoceptors," Naunyn-Schmiedeberg's Arch. Pharmacol., vol. 374, pp. 385-398, 2007.

* cited by examiner

Primary Examiner — Irina Neagu
(74) Attorney, Agent, or Firm — McCarter & English, LLP; Jill Ann Mello

(57) ABSTRACT

The invention relates to the use of selective agonists of beta-3 adrenergic receptors for the treatment and/or prevention of pulmonary hypertension.

9 Claims, 6 Drawing Sheets

BETA-3 ADRENOCEPTOR AGONISTS FOR THE TREATMENT OF PULMONARY HYPERTENSION

RELATED APPLICATIONS

This application is a 35 U.S.C. § 371 national stage filing of International Application No. PCT/ES2013/070611, filed on Aug. 28, 2013, which claims priority to Spanish Patent Application No. P201231343, filed on Aug. 29, 2012. The entire contents of each of the foregoing applications are incorporated herein by reference.

FIELD OF THE INVENTION

The present invention is comprised within the field of medicine, more particularly, it relates to treating pulmonary hypertension.

BACKGROUND OF THE INVENTION

Pulmonary hypertension (PH), defined as the increase of mean pulmonary artery pressure (PAP) above normal values, encompasses a series of diseases characterized by the increase of pulmonary vascular resistances (PVRs) and progressive deterioration of the right ventricle (RV) function (McLaughlin 2009). In this regard, most studies refer to PH for mean PAP values above 25 mmHg, considering that a typical mean PAP in humans is about 12 to 15 mmHg.

There are many causes of PH which have been classified into 5 groups: pulmonary arterial hypertension (PAH); PH due to left heart disease; PH due to lung disease; chronic thromboembolic PH; and PH of an unknown or multifactorial origin. Unlike other groups, PH due to left heart disease is of a post-capillary origin, characterized by the increase of pulmonary capillary pressure.

The incidence of PH in the population is high and it is associated with high morbidity and mortality. Approximately two thirds of patients with left ventricular dysfunction (isolated diastolic or systolic) develop PH.

Currently, there is a lack of treatments for PH. Advances in the development of new pharmacological therapies have focused on idiopathic PH, the least frequent subgroup (prevalence of 6 cases per million people). In this subgroup the first line treatment is calcium-antagonists, which are only effective over the long term in 1% of the cases. Other treatments using vasodilators, such as prostaglandins (Barst 1996), 5-phosphodiesterase inhibitors (Galié 2005) or endothelin receptor antagonists (Channick 2001), provide benefits in a higher percentage of patients, although their clinical and hemodynamic effect is small (mean PAH reduction of 2-10%). In addition, these treatments have not proven consistent efficiency in pulmonary hypertension due to a left cardiac pathology (the most frequent), nor in the remaining pulmonary hypertension groups generally.

There has been little research on β3 adrenergic receptors in the field of cardiovascular diseases. Stimulation of these receptors is associated with the production of nitric oxide and the relaxation of vascular tone. In a study with rat lung samples, stimulation of β3 adrenergic receptors produced dose-dependent relaxation (Dumas 1998). In a functional study of rings of pulmonary artery extracted from dogs, an increase of relaxation with selective stimulation of β1, β2 and β3 adrenergic receptors was observed (Tagaya 1999). However, in another study in which pulmonary arteries were extracted from control mice and from mice with hypoxia-induced PH, increase of relaxation with selective stimulation of β3 receptors was not observed (Leblais, 2008).

LITERATURE REFERENCES

McLaughlin V V, Archer S L, Badesch D B, Barst R J, Farber H W, Lindner J R, Mathier M A, McGoon M D, Park M H, Rosenson R S, Rubin L J, Tapson V F, Varga J, Harrington R A, Anderson J L, Bates E R, Bridges C R, Eisenberg M J, Ferrari V A, Grines C L, Hlatky M A, Jacobs A K, Kaul 5, Lichtenberg R C, Moliterno D J, Mukherjee D, Pohost G M, Schofield R S, Shubrooks S J, Stein J H, Tracy C M, Weitz H H, Wesley D J. ACCF/AHA 2009 expert consensus document on pulmonary hypertension: a report of the American College of Cardiology Foundation Task Force on Expert Consensus Documents and the American Heart Association: developed in collaboration with the American College of Chest Physicians, American Thoracic Society, Inc., and the Pulmonary Hypertension Association. Circulation 2009; 119: 2250-2294.

Barst R J, Rubin L J, Long W A, McGoon M D, Rich S, Badesch D B, Groves B M, Tapson V F, Bourge R C, Brundage B H, et al. A comparison of continuous intravenous epoprostenol (prostacyclin) with conventional therapy for primary pulmonary hypertension. The Primary Pulmonary Hypertension Study Group. N Engl J Med. 1996 Feb. 1; 334(5):296-302. PubMed PMID: 8532025.

Nazzareno Galiè, M.D., Hossein A. Ghofrani, M.D., Adam Torbicki, M.D., Robyn J. Barst, M.D., Lewis J. Rubin, M.D., David Badesch, M.D., Thomas Fleming, Ph.D., Tamiza Parpia, Ph.D., Gary Burgess, M.D., Angelo Branzi, M.D., Friedrich Grimminger, M.D., Marcin Kurzyna, M.D., and Gérald Simonneau, M.D., for the Sildenafil Use in Pulmonary Arterial Hypertension (SU-PER) Study Group. Sildenafil Citrate Therapy for Pulmonary Arterial Hypertension. N Engl J Med 2005; 353: 2148-57.

Richard N Channick, Gérald Simonneau, Olivier Sitbon, Ivan M Robbins, Adaani Frost, Victor F Tapson, David B Badesch, Sébastien Roux, Maurizio Rainisio, Frederic Bodin, Lewis J Rubin. Effects of the dual endothelin-receptor antagonist bosentan in patients with pulmonary hypertension: a randomised placebo-controlled study. Lancet 2001; 358: 1119-23.

Dumas M, Dumas J-P, Bardou M, Rochette L, Advenier C, Giudicelli J-F (1998) Influence of β-adrenoceptor agonists on the pulmonary circulation. Effects of a β3-adrenoceptor antagonist, SR 59230A. Eur J Pharmacol 348: 223-228.

Tagaya E, Tamaoki J, Takemura H, Isono K, Nagai A (1999) Atypical adrenoceptor-mediated relaxation of canine pulmonary artery through a cyclic adenosine monophosphate-dependent pathway. Lung 177:321-332.

Leblais V, Estelle D, Fresquet F, Bégueret H, Bellance N, Banquet S, Allières C, Leroux L, Desgranges C, Gadeau A, Muller B (2008) β-adrenergic relaxation in pulmonary arteries: preservation of the endothelial nitric oxide-dependent β2 component in pulmonary hypertension. Cardiovasc Res 77: 202-210.

The problem of treating pulmonary hypertension is still far from being satisfactorily resolved and therefore the need to develop new therapies for treating said disease still exists.

BRIEF DESCRIPTION OF THE INVENTION

The authors of the present invention have satisfactorily found that selective stimulation of beta-3 adrenergic receptors has a beneficial effect in the pulmonary hypertension (PH). It has therefore been observed that the administration of selective beta-3 adrenergic receptor agonists in chronic PH and acute PH models elicits a favorable response to said disease: reduction of pulmonary pressure, increase of oxygen saturation, reduction of pulmonary vascular resistances, etc. Likewise, compared to other vasodilators commonly used in this disease, selective beta-3 adrenergic receptor agonists do not produce significant changes in systemic blood pressure or in the heart rate, possible side effects detrimental to systemic circulation therefore being minimized.

Therefore, in one aspect the invention relates to the use of a selective beta-3 adrenergic receptor agonist for preparing a medicinal product for treating and/or preventing PH.

In another aspect, the invention relates to a selective beta-3 adrenergic receptor agonist for use in treating and/or preventing PH.

In another aspect, the invention relates to the use of a selective beta-3 adrenergic receptor agonist for treating and/or preventing PH.

In another aspect, the invention relates to a medicinal product or pharmaceutical composition comprising at least one selective beta-3 adrenergic receptor agonist and at least one pharmaceutically acceptable excipient for use in treating and/or preventing PH.

Another aspect of the invention is a method for treating and/or preventing PH, which comprises administering to the patient in need of a treatment or prevention of this type a therapeutically effective amount of a selective beta-3 adrenergic receptor agonist.

These aspects and preferred embodiments thereof are also additionally defined below in the detailed description and in the claims.

DETAILED DESCRIPTION OF THE INVENTION

Figure 1:
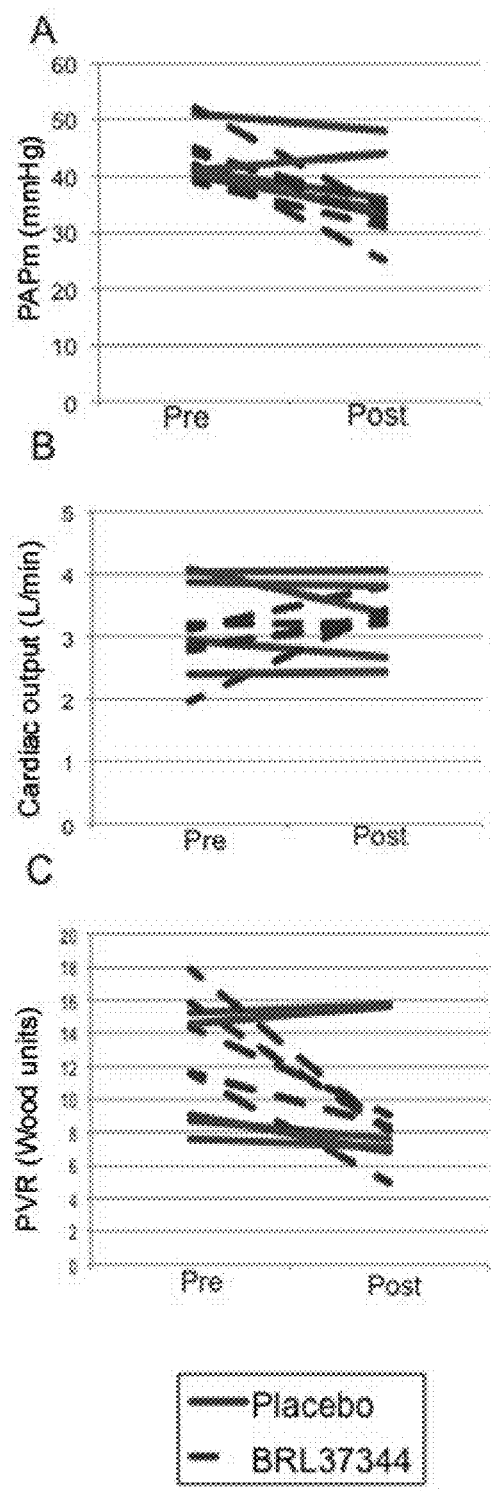
FIG. 1 shows pre- and 10-minute post-treatment changes (placebo represented by a solid line and BRL37344 by a discontinuous line) in mean PAP (A), cardiac output (B) and PVR (C) in 10 animals with acute PH.

The present inventors have found that a well-known group of biologically active compounds, namely selective beta-3 adrenergic receptor agonists, are useful for preparing medicinal products aimed at treating and/or preventing pulmonary hypertension (PH) in mammals, including humans.

To provide a more concise description, some of the quantitative expressions provided herein are not qualified with the term "about". It is understood that, whether or not the term "about" is used explicitly, any amount given herein seeks to refer to the actual given value, and it also seeks to refer to the approximation to such given value which would be reasonably deduced based on common know-how in the art, including equivalents and approximations due to the experimental and/or measurement conditions for such given value.

For the sake of simplicity, "selective β3 agonist", "selective beta-3 agonist" or similar expressions are used herein to refer to a "selective beta-3 adrenergic receptor agonist".

Generally, an agonist is a molecule that binds to the receptor and has an intrinsic effect, and therefore increases the basal activity of a receptor when it comes into contact with the receptor. In the present invention, selective beta-3 adrenergic receptor agonist is understood as a compound that exhibits preferential agonism towards the beta-3 receptor compared to the beta-1 and beta-2 receptors. Therefore the selective beta-3 agonists behave like beta-3 receptor agonists at lower concentrations than for beta-1 and beta-2 receptors. A selective beta-3 agonist also includes compounds that behave like beta-3 receptor agonists and like beta-1 and beta-2 receptor antagonists.

Preferably, the selectivity of the useful compounds in the present invention towards the beta-3 receptor is clearly higher compared to beta-1 and beta-2 receptors. In a preferred embodiment, the selective β3 agonists according to the present invention show selectivity towards the beta-3 receptor that is about ≥10 times higher, more preferably about ≥100 times higher, and still more preferably about ≥1000 times higher, with respect to other beta adrenergic receptors. Even more preferably for the purpose of the invention, selective β3 agonists show selectivity towards the beta-3 receptor that is "infinitely" higher (about ≥10000 times) with respect to other beta adrenergic receptors. In preferred particular embodiments, the selective β3 agonist shows inhibition constant and/or mean effective concentration values for β3, β1 and β2 receptors, respectively, of about Ki 287/1750/1120 nM and/or $EC_{50}$ 18/>10000/>10000 nM. The capability of a specific compound to exert selective beta-3 agonism can be easily evaluated by means of conventional techniques. General literature references related to receptor ligand-binding assays include, for example: Masood N. Khan, John W. Findlay (2010). Ligand-Binding Assays: Development, Validation, and Implementation in the Drug Development Arena: John Wiley & Sons; *Assay Guidance Manual Version 5.0*, 2008: Eli Lilly and Company and NIH Chemical Genomics Center, available at: http://ncgcweb.nhgri.nih.gov/guidance/manual_toc.html.

Representative examples of selective beta-3 agonists useful in the present invention include, but are not limited to:
BRL 37344
CL 316243
AZ 002
BMS 187257
L-755507
L-750355
FR-149175
GW427353 (Solabegron)
YM178 (Mirabegron)
CR 58611
SR 58611A (Amibegron)
SR 59104A
SR 59119A
and their pharmaceutically acceptable salts.

Any compound to which reference is made herein seeks to represent such specific compound as well as certain variations or forms. Therefore the useful compounds in the present invention can be, for example, in neutral form, in the form of a base or acid, in the form of a salt, preferably a physiologically acceptable salt, in the form of a solvate or of a polymorph and/or in different isomeric forms.

The term "salt" must be understood as any form of an active compound used according to this invention in which said compound is in ionic form or is charged and coupled to a counterion (a cation or anion) or is in solution. This definition also includes quaternary ammonium salts and active molecule complexes with other molecules and ions, particularly complexes formed by means of ionic interactions. The definition particularly includes physiologically acceptable salts; this term must be understood as equivalent to "pharmacologically acceptable salts" or "pharmaceutically acceptable salts".

The expression "physiologically acceptable salt" or "pharmaceutically acceptable salt" is particularly understood in the context of this invention as a salt (as defined above) formed either with a acid that is physiologically tolerated, i.e., salts of the particular active compound with organic or inorganic acids that are physiologically tolerated, particularly if they are used in human beings and/or mammals, or with at least one cation, preferably an inorganic cation, that is physiologically tolerated, particularly if they are used in human beings and/or mammals. Examples of particular acid salts that are physiologically tolerated are: hydrochloric acid, hydrobromic acid, sulfuric acid, hydrobromide, monohydrobromide, monohydrochloride or hydrochloride, methiodide, methanesulfonic acid, formic acid, acetic acid, oxalic acid, succinic acid, malic acid, tartaric acid, mandelic acid, fumaric acid, lactic acid, citric acid, glutamic acid, hippuric acid, picric acid and/or aspartic acid salts. Examples of particular base salts that are physiologically tolerated are alkali metal and alkaline-earth metal salts and with $NH_4$.

According to this invention, the term "solvate" must be understood to mean any form of the active compound according to the invention in which this compound binds to another molecule (usually a polar solvent) by means of a non-covalent bond, particularly including hydrates and alcoholates, such as methanolate, for example.

Also within the scope of the invention is any compound which is a prodrug of a selective beta-3 adrenergic receptor agonist. The term "prodrug" is used in the broadest sense of the word and covers those derivatives converted into the compounds of the invention in vivo. Examples of prodrugs include, but are not limited to, derivatives and metabolites of selective beta-3 agonist compounds, including biohydrolyzable residues such as biohydrolyzable amides, biohydrolyzable esters, biohydrolyzable carbamates, biohydrolyzable carbonates, biohydrolyzable ureides and biohydrolyzable phosphate analogues. Prodrugs of compounds with functional carboxyl groups are preferably lower alkyl esters of carboxylic acid. Carboxylate esters are suitably formed by esterifying any of the carboxylic acid residues present in the molecule. Prodrugs can usually be prepared using well-known methods, such as those described in Burguer "Medicinal Chemistry and Drug Discovery $6^{th}$ ed." (Donald J. Abraham ed. 2001, Wiley), "Design and Applications of Prodrugs" (H. Bundgaard ed., 1985, Harwood Academic Publishers) and Krogsgaard-Larsen et al. "Textbook of Drug Design and Discovery" Taylor & Francis (April 2002).

Selective beta-3 agonists useful in the present invention can include optical isomers depending on the presence of chiral centers or geometric isomers depending on the presence of multiple bonds (for example Z, E). Individual isomers, enantiomers or diastereoisomers and mixtures thereof, such as a racemic mixture are within the scope of the present invention.

Furthermore, any compound to which reference is made herein can exist as tautomers. Specifically, the term tautomer refers to one of two or more structural isomers of a compound in equilibrium and easily converted from one isomeric form to another. Common tautomeric pairs are amine-imine, amide-imidic acid, keto-enol, lactam-lactim, etc.

Unless otherwise indicated, it also is understood that the compounds of the invention include isotopically labeled forms, i.e., compounds differing only by the presence of one or more isotopically enriched atoms. For example, compounds having the present structures except the substitution of at least one hydrogen atom with a deuterium or tritium atom, or the substitution of at least one carbon with a $^{13}$C- or $^{14}$C-enriched carbon, or the substitution of at least one nitrogen with $^{15}$N-enriched nitrogen, are within the scope of this invention.

Selective beta-3 agonists in the context of the invention are preferably in a pharmaceutically acceptable or substantially pure form. Pharmaceutically acceptable form is understood, among others, to have a pharmaceutically acceptable purity level excluding typical pharmaceutical additives such as diluents and vehicles, and to not include any material considered toxic at normal dosage levels. Purity levels with respect to the active ingredient are preferably greater than 50%, more preferably greater than 70%, most preferably greater than 90%. In a preferred embodiment, it is greater than 95% selective beta-3 agonist.

As observed above, the expression "pharmaceutically acceptable prodrugs, solvates or salts" refers to any salt, solvate or any other compound which, after administration to the recipient, can (directly or indirectly) provide a selective beta-3 agonist. It will be observed that non-pharmaceutically acceptable prodrugs, solvates and salts are also within the scope of the invention given that they can be useful in preparing pharmaceutically acceptable prodrugs, solvates and salts. Prodrugs, solvates and salts can be prepared by means of methods known in the art.

In a particular embodiment of the invention, the selective beta-3 agonist is selected from a compound derived from phenylethanolamine (2-amino-1-phenylethanol).

More particularly, the selective beta-3 agonist is selected from a compound derived from phenylethanolamine, with the following general formula:

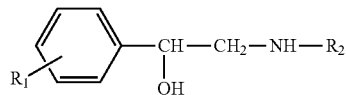

wherein $R_1$ and $R_2$ can represent various meanings, as detailed below.

In a more particular embodiment, $R_1$ is selected from hydrogen and halogen (F, Cl, Br or I); the halogen is preferably chlorine. $R_1$ can be in any position (ortho, meta or para); in a preferred embodiment, $R_1$ is in the meta position.

In another more particular embodiment, R$_2$ is an aralkyl, being able to be substituted in the aryl part and/or in the alkyl part, or a radical selected from:

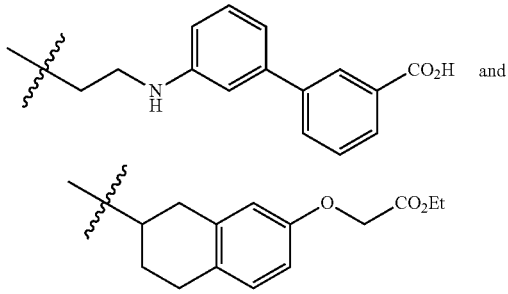

Particular R$_2$ radicals are indicated below:

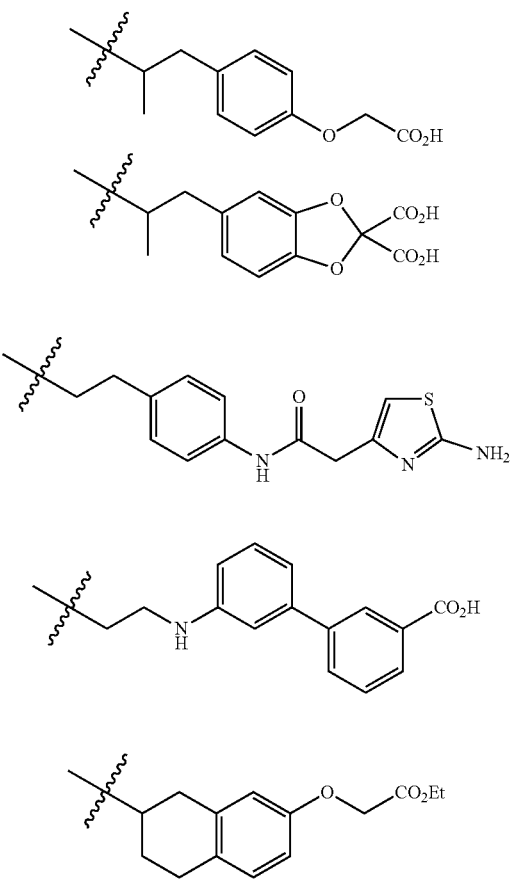

In a preferred embodiment, R$_1$ represents chlorine in meta position and R$_2$ is an optionally phenyl-substituted 1-methyl-2-phenylethyl radical.

In another preferred embodiment, R$_1$ represents hydrogen and R$_2$ is an optionally phenyl-substituted 2-phenylethyl radical. In a preferred embodiment, the agonist used in the present invention is the compound identified as BRL37344 ([4-[(2R)-2-[[(2R)-2-(3-clorophenyl)-2-hydroxyethyl]amino]propyl]phenoxy]acetic acid), which is described in documents EP 023 385 and in Drugs of the Future, Vol. 16, 797-800 (1991), and it has the following molecular formula:

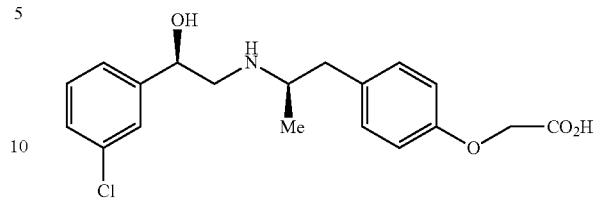

Compound BRL 37344 is a potent and selective beta-3 adrenergic receptor agonist (Ki values are 287, 1750 and 1120 nM for β3, β1 and β2 receptors, respectively) which can be commercially acquired in the form of sodium salt (CAS number 127299-93-8):

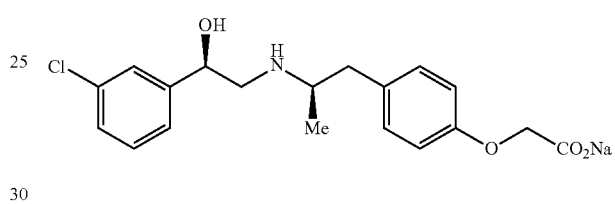

In another embodiment of the invention, the compound known as CL316243 is preferred, said compound being described in documents EP 0 455 006 and J. Med. Chem., Vol. 35, 3081-3084 (1992) and having the following molecular formula:

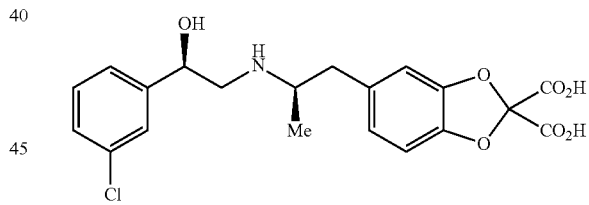

Compound CL 316243 is a potent and selective beta-3 adrenergic receptor agonist (EC$_{50}$=3 nM; selectivity 10000 orders of magnitude greater than β1 and β2) which can be commercially acquired in the form of disodium salt (151126-84-0):

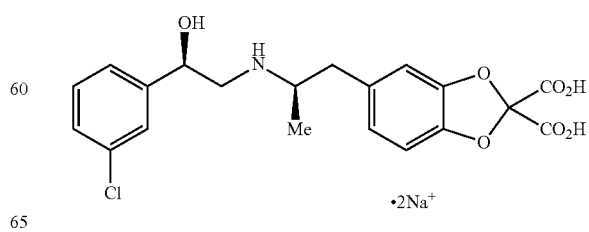

In another preferred embodiment, the agonist used in the present invention is YM178 (Mirabegron) or a salt thereof. Mirabegron is a compound marketed for treating hyperactive bladder and has the following molecular formula:

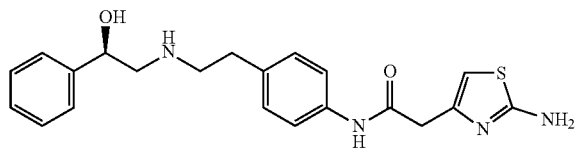 [SMILES: Nc1nc(CC(=O)Nc2ccc(CCNC[C@H](O)c3ccccc3)cc2)cs1]

In another preferred embodiment, the agonist used in the present invention is GW427353 (Solabegron) or a salt thereof, such as its hydrochloride. Solabegron has the following molecular formula:

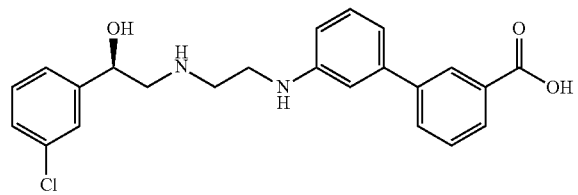 [SMILES: O=C(O)c1cccc(-c2cccc(NCCNC[C@H](O)c3cccc(Cl)c3)c2)c1]

In another preferred embodiment, the agonist used in the present invention is SR 58611A (Amibegron) or a salt thereof. Amibegron is an antidepressant that has the following molecular formula:

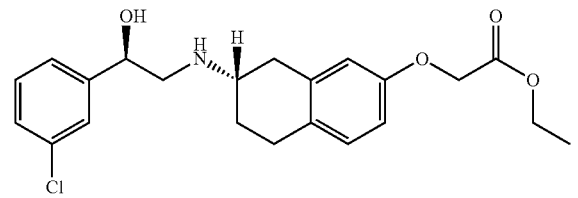 [SMILES: CCOC(=O)COc1ccc2c(c1)C[C@@H](NC[C@H](O)c1cccc(Cl)c1)CC2]

Other documents describing compound BRL 37344 and more compounds showing agonism towards beta-3 adrenergic receptor are: US20040242485A1, U.S. Pat. Nos. 4,873,240, 4,880,834, 5,002,946, 5,087,626, 5,236,951, 5,578,638, 6,172,099, 6,187,809.

Additional compounds known to show selective agonist activity for beta-3 adrenergic receptors are described, for example, in patent documents: U.S. Pat. Nos. 4,396,627, 4,478,849, 4,999,377, 5,153,210, WO98/32753, WO97/46556, WO97/37646, WO97/15549, WO97/25311, WO96/16938, WO95/29159, WO02/06276, EP427480, EP659737, EP801060, EP714883, EP764632, EP764640, EP827746, U.S. Pat. Nos. 5,561,142, 5,705,515, 5,436,257, 5,578,620 and 6,537,994.

The person skilled in the art can easily determine if a compound is useful for the purpose of the invention. Therefore, as indicated above, there are conventional methods suitable for assessing if a compound is a good selective beta-3 adrenergic receptor agonist. Furthermore, both the determination of beta-3 agonist activity and of beta-3 receptor selectivity with respect to beta-1/beta-2 receptors can be evaluated following previously established specific functional assays such as those described in the aforementioned patents and applications, particularly WO98/32753, WO97/46556, EP764632, EP764640, and EP827746.

As indicated above, selective beta-3 adrenergic receptor agonists are commercially available and/or can be prepared by known methods, such as those described, for example, in the aforementioned patents and applications.

Pharmaceutical Compositions

The inventors have demonstrated in different scenarios that the administration of selective beta-3 agonists allows significantly reducing pulmonary artery pressure as well as pulmonary vascular resistances, in turn increasing oxygen saturation. As an additional advantage, significant changes are not observed in cardiac output or in systemic blood pressure, which means that the possible side effects detrimental to systemic circulation are very low compared to other vasodilators used for treating pulmonary hypertension.

The present invention therefore proposes the use of selective beta-3 adrenergic receptor agonists as a broad spectrum therapeutic agent against pulmonary hypertension (PH). Therefore, the results obtained prove the enormous usefulness of selective beta-3 agonists in treating and/or preventing PH of any etiology. In the context of the present invention, the PH can be of any type: pulmonary arterial hypertension (PAH); PH due to left heart disease; PH due to lung disease; chronic thromboembolic PH; and PH of an unknown or multifactorial origin.

According to a particular embodiment, the invention relates to the use of a selective beta-3 adrenergic receptor agonist for treating and/or preventing acute PH. According to another particular embodiment, the invention relates to the use of a selective beta-3 adrenergic receptor agonist for treating and/or preventing chronic PH. In a more particular embodiment, the invention relates to the use of a selective beta-3 adrenergic receptor agonist under an acute pulmonary thromboembolism scenario.

Medicinal products or pharmaceutical compositions for use in treating and/or preventing PH comprising a selective beta-3 adrenergic receptor agonist and a pharmaceutically acceptable excipient are provided with this invention.

Examples of pharmaceutical compositions include any solid (tablets, pills, capsules, granules, etc.) or liquid (solutions, suspensions or emulsions) composition for oral, topical or parenteral administration.

The term "excipient" refers to components of a pharmacological compound other than the active ingredient (definition obtained from the European Medicines Agency—EMA). They preferably include a "carrier, adjuvant and/or vehicle". Carriers are forms in which substances are incorporated to improve drug administration and efficacy. Drug carriers are used in drug administration systems such as controlled release technology to prolong the actions of the drug in vivo, reduce drug metabolism and reduce drug toxicity. Carriers are also used in designs to increase the efficacy of drug administration to pharmacological target action sites (U.S. National Library of Medicine. National Institutes of Health). Adjuvant is a substance added to a pharmacological product formulation affecting the action of the active ingredient in a predictable manner. Vehicle is an excipient or a substance, preferably without any therapeutic action, used as a means to provide volume for the administration of medicinal products (Stedman's Medical Spellchecker, © 2006 Lippincott Williams & Wilkins). Such pharmaceutical carriers, adjuvants or vehicles can be sterile liquids, such as water and oils, including petroleum oil or oil of an animal, plant or synthetic origin, such as peanut oil, soybean oil, mineral oil, sesame seed oil and the like, excipients, disintegrants, wetting agents or diluents. Suitable pharmaceutical carriers are described in "Remington's Pharmaceutical Sciences" by E. W. Martin. The selection of these excipients and the amounts to be used will depend on the form of application of the pharmaceutical composition.

The daily dosage for human beings and animals can vary depending on factors based on the respective species or other factors, such as age, sex, weight or degree of disease, etc. The daily dosage for human beings can preferably be in the range of from 1 to 2000, preferably from 1 to 1500, more preferably from 1 to 1000 milligrams of active ingredient to be administered in one or several doses a day.

The formulations can be prepared according to conventional methods such as those described in the Spanish, European or US Pharmacopoeias, or in similar reference texts, for example "Tratado de Farmacia Galénica", by C. Fauli i Trillo, 10$^{th}$ Edition, 1993, Luzán 5, S.A. de Ediciones.

The compounds and compositions of this invention can be used with other drugs to provide a combination therapy. The other drugs can be part of the same composition or can be provided as a separate composition for administration at the same time or at a different time.

As it is used herein, the terms "to treat", "treating" and "treatment" generally include the eradication, elimination, reversal, alleviation, modification or control of PH in a subject.

As it is used herein, the terms "prevention", "preventing", "preventive", "to prevent" and prophylaxis refer to the capability of a given substance to thwart, minimize or complicate the onset or development of PH in a subject.

The term "subject" or "patient" in the context of the invention includes any animal, particularly vertebrate animals, preferably mammals, such as mice, rats, horses, pigs, rabbits, cats, sheep, dogs, cows, human beings, etc. In a preferred embodiment, the mammal is a pig or a human being. In another even more preferred embodiment, the mammal is a human being.

The invention is described below by means of the following examples which must be considered as merely illustration and non-limiting thereof.

EXAMPLES

Methods

Generating the Experimental Models
Acute PH:

In 10 2 month old healthy pigs (weighing ≈30 kg) anesthetized, intubated and ventilated with 40% FiO$_2$, while continuously monitoring blood pressure, heart rate (HR), oxygen saturation as well as PAP and repeated measurements of cardiac output (CO) by means of thermodilution using a Swan-Ganz catheter, acute PH was generated by means of pulmonary embolization with a suspension of microspheres (Sephadex G50 coarse; Pharmacia Biotech; Freiburg, Germany) by femoral vein route. The dose necessary for causing an increase of mean PAP≥40 mmHg to remain stable for 10 minutes was administered. At that time the animals were randomized to receive specific β3 agonist BRL37344 (5 µg/Kg) or physiological saline (vehicle).
Chronic PH:

For the purpose of reproducing a broad spectrum of PH in the general population, 2 experimental models of chronic PH were developed: a pre-capillary model which would represent clinical groups 1, 3, 4 and 5; and a post-capillary model which would characterize clinical group 2 (revised WHO Classification).
Pre-Capillary PH Model The pre-capillary PH model was generated by means of pulmonary arterial embolization with synthetic microspheres 300 microns in diameter (Sephadex G50 coarse; Pharmacia Biotech; Freiburg, Germany), a variant of a model previously described (Bernd W. Bottiger, MD; Johann Motsch, MD; Joachim Dorsam, MD; UlfMieck, MD; Andre Gries, MD, forg Weimann, MD; and Eike Martin, MD. Inhaled Nitric Oxide Selectively Decreases Pulmonary Artery Pressure and Pulmonary Vascular Resistance Following Acute Massive Pulmonary Microembolism in Piglets. CHEST1996; 110:1041-47).

The protocol was initiated in 3 month old Large-White pigs, *Sus scrofa* species (weighing ≈40 kg). After general anesthesia and analgesia and under cardiac monitoring and orotracheal intubation, the femoral vein and artery were cannulated by means of percutaneous puncture in the cardiac hemodynamics laboratory. Through the venous access, a Swan-Ganz catheter was placed in one of the main branches of the pulmonary artery (PA), which was connected to a monitor to continuously record PAP and to quantify pulmonary capillary pressure and cardiac output. The arterial route allowed continuously recording systemic blood pressure. Venous access served to administer the microspheres towards the pulmonary arterial circulation. A solution was prepared with 500 mg of microspheres in 200 ml of physiological saline and the amount necessary to reach mean sustained PAP>40 mmHg in about 20 minutes was administered. This method was repeated weekly (3-5 embolizations) until generating chronic PH (mean PAP>25 mmHg at rest). Two-month follow-up was conducted on the animals. At the end of the follow-up, the animals were euthanized and their hearts extracted for histological analysis. The histopathological lesions observed in the lung reproduce those shown in arterial PH or chronic thromboembolic PH in humans: arterial intima proliferation with media hypertrophy and perivascular fibrosis, vascular occlusions, and complex lesions such as vascular aneurisms or plexiform lesions.
Post-Capillary PH Model The post-capillary PH model was generated by means of the non-restrictive surgical cerclage of the main pulmonary vein in 4 week old piglets (weighing about 10 kg). This vein drains the blood from both lower lung lobes, forming about 80% of the pulmonary mass. With analgesia and general anesthesia and under cardiac monitoring and orotraqueal intubation, the right external jugular vein and common carotid artery were located by means of surgical dissection. The Swan-Ganz catheter was introduced through the venous access to continuously monitor PAP, pulmonary capillary pressure and cardiac output. The arterial route also served to monitor systemic blood pressure during the surgical intervention. By means of right lateral thoracotomy through the fifth intercostal space, non-restrictive cerclage of the main pulmonary vein was performed by means of placing a 5 mm wide polyester band around the vessel fitting the at-rest diameter of the pulmonary venous confluence right before it enters the left atrium. This method prevented causing post-surgical acute lung edema because pulmonary vein stenosis is not present immediately after surgery but rather progresses as the animal grows. It is therefore a progressive PH model (severity intensifies throughout follow-up). In this study, significant PH was observed 4 weeks after surgery (mean PAP=35±5 mmHg), associated with dilatation and hypertrophy of the RV and without perioperative mortality. At the end of follow-up, the animals were euthanized and their hearts extracted for histological analysis. The histological lesions observed reproduce those of PH due to left heart disease or congenital stenosis of the pulmonary veins, and include arterial and venous vessels remodeling within the pulmonary parenchyma, intima proliferation and primary PA media hypertrophy and clear myocardiocyte hypertrophy in the RV, where an increase of fibrosis and myocardial disorganization is further seen.

Right Heart Catheterization

The hemodynamic study was conducted by means of right heart catheterization strictly using the same methodology as in humans. Once PH was generated, the following parameters were quantified basally and after the administration of the β3 agonist, in duplicate: PAP, pulmonary capillary pressure and right atrial pressure. Cardiac output was quantified by the thermodilution technique. Five measurements were taken, and the mean of 3 measurements was considered after excluding the highest and lowest determinations. Left ventricular end-diastolic pressure was determined by means of placement of a pig-tail catheter inside the left ventricle through the femoral artery. Pulmonary vascular resistances were calculated as the difference between mean PAP and left ventricular end-diastolic pressure divided by the cardiac output and expressed in Wood units.

An echocardiogram was performed prior to heart catheterization to confirm the absence of significant valvular diseases or intracardiac shunts that may invalidate the cardiac output measurements by means of thermodilution.

Administration of β3 Agonists

To evaluate the effect of a single dose of BRL 37344 (in the form of sodium salt) 5 μg/Kg of the drug diluted in physiological saline was administered in all cases by endovenous route. This dose was established after a pilot study intended for selecting the maximum dose that does not generate a systemic hemodynamic involvement (to avoid possible side effects). The effect of the drug was evaluated 10 minutes after administration in acute PH and 20 minutes after administration in chronic PH.

To evaluate the chronic effect of the administration of BRL 37344, a cohort of animals with post-capillary PH was randomized into BRL 37344 or placebo (physiological saline). A subcutaneous osmotic pump (Alzet 2 ml) coupled to a vascular catheter inserted in the internal jugular vein was implanted in all the animals. Those animals randomized into BRL 37344 received a dose of 10 μg/Kg/day for 14 days. The hemodynamic change was blindly evaluated after 2 weeks of follow-up.

To evaluate the chronic effect of treatment with Mirabegron, a 50 mg tablet was administered orally every 12 hours in all cases. The fixed dose for all the animals was based on doses used in humans for different pathologies (never PH because it has never been tested in this entity), resulting in no adverse effects. The dose used for treating neurogenic bladder is 25 to 50 mg/day, whereas in studies designed to evaluate the effect of this drug in heart failure (see "Beta 3 Agonist Treatment in Heart Failure (Beat-HF) NCT01876433"), the expected initial dose is 25 mg/12 hours, being titrated to a maximum of 150 mg/12 hours. The dose of 50 mg/12 hours intends to be an average dose that can be easily extrapolated to patients with whom an efficacy study could be conducted knowing that the side effect profile is favorable.

Statistical Analysis

The continuous variables are expressed as mean±SD and qualitative variables are expressed as frequency (%). The comparison between the intervention groups with respect to changes in the variables, calculated as the difference between the post-treatment and pre-treatment value (both in acute PH and chronic PH), was performed by means of the Wilcoxon test. The evaluation of the effect of a single dose of β3 agonist on the hemodynamic parameters in chronic PH was performed by means of the Student's T test or Wilcoxon test for paired data, according to the distribution of the variables. A value of $P<0.05$ was considered significant.

Results

1. Effect of a Single Dose of BRL37344 in Acute PH Due to Pulmonary Embolism

The baseline characteristics of animals after pulmonary embolization did not differ between the groups randomized into β3 agonist BRL37344 (5 μg/Kg) or placebo (Table 1).

TABLE 1

Post-pulmonary embolization baseline characteristics of animals randomized into BRL37344 or physiological saline.

|  | Control group (N = 5) | Group with BRL37344 (N = 5) | P |
|---|---|---|---|
| Weight (Kg) | 29.2 ± 1.4 | 28.4 ± 3.8 | 0.69 |
| $O_2$ saturation (%) | 90.4 ± 5.3 | 89.6 ± 5.0 | 0.69 |
| Heart rate (bpm) | 98.2 ± 13.3 | 100.2 ± 13.9 | 0.69 |
| Mean blood pressure (mmHg) | 91.4 ± 10.9 | 91.2 ± 15.3 | 1.00 |
| Mean pulmonary artery pressure (mmHg) | 42.8 ± 4.6 | 44.4 ± 4.8 | 0.42 |
| Cardiac output (L/min) | 3.5 ± 0.8 | 2.8 ± 0.5 | 0.22 |
| Pulmonary vascular resistances (WU) | 11.0 ± 3.6 | 14.2 ± 2.7 | 0.22 |

Ten minutes after administration, the group treated with BRL37344 showed a significant reduction of PAPm (−13.0±4.5 vs. −3.8±4.2; p=0.008), PVR (−6.5±2.4 vs. −0.4±1.3; p=0.008) and increase of CO (0.62±0.53 vs. −0.20±0.31; p=0.008). FIG. 1 shows the individual values of these 3 parameters. No significant differences were observed in the variation of HR (−4.4±14.1 vs. −3.0±7.1; p=0.84) or mean systemic blood pressure (−4.6±8.0 vs. 1.0±7.4; p=0.31).

2. Effect of a Single Dose of BRL 37344 in Chronic Pre- and Post-Capillary PH

Figure 2:
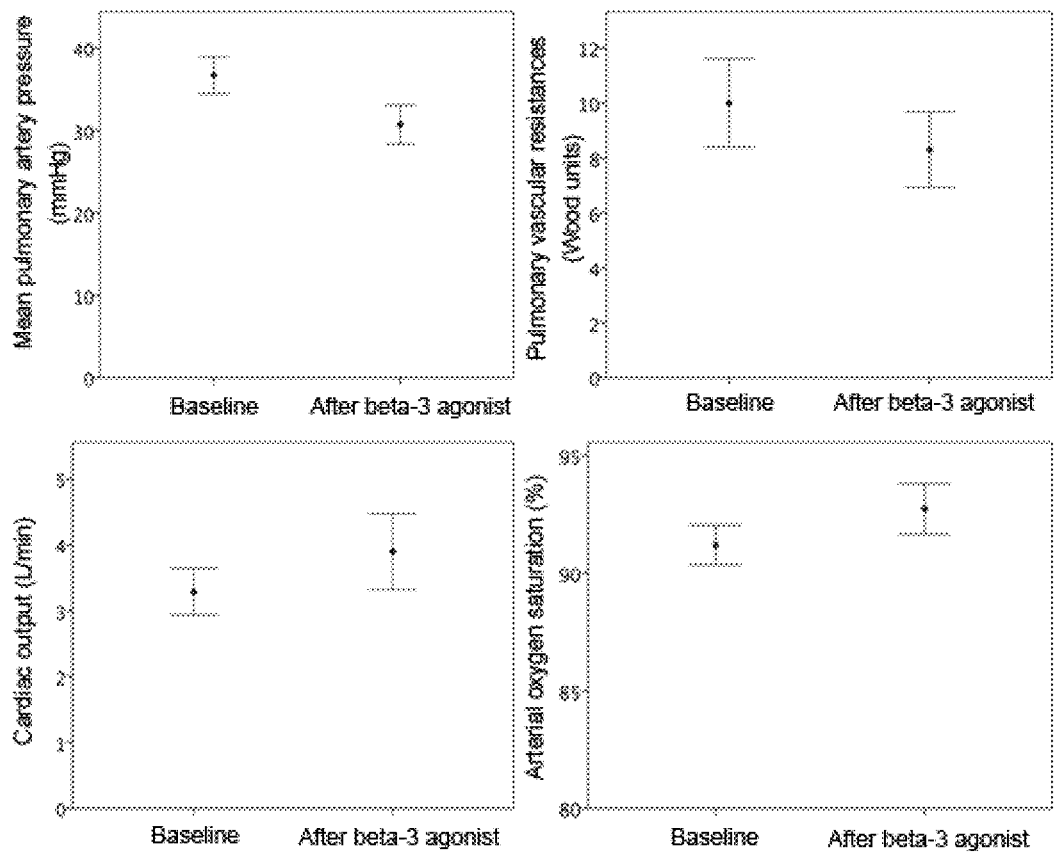
FIG. 2 shows the effect of the administration of BRL 37344 on mean PAP, PVR, cardiac output and arterial oxygen saturation (mean±standard error) in post-capillary chronic PH.

In chronic post-capillary PH (that which is associated with heart disease), the administration of the selective β3 adrenergic agonist BRL 37344 was associated with a 30% reduction of the mean PAP (FIG. 2). The mean PAP decreased from 37.6±9.8 to 28.8±9.8 mmHg (p<0.001). A 23% reduction of systolic pulmonary pressure (50.6±15.5 to 38.9±9.9 mmHg, p<0.001) was also observed.

Administration of the agonist was also associated with an 18% increase of the cardiac output (3.29±0.9 to 3.90±1.5 L/min, p=0.07), a 36% reduction of pulmonary vascular resistances (10.0±4.3 to 6.4±3.2 Wood units, p=0.002) and a 3.2% increase of oxygen saturation (90.88±2.64 to 93.75±3.01%, p=0.001).

Finally, after administration of the selective β3 adrenergic agonist no significant changes were observed in systemic blood pressure (85.7±13.9 to 79.9±6.9 mmHg, p=0.11), or in heart rate (83.8±21.1 to 87.8±16.8 bpm, p=0.20).

Figure 3:
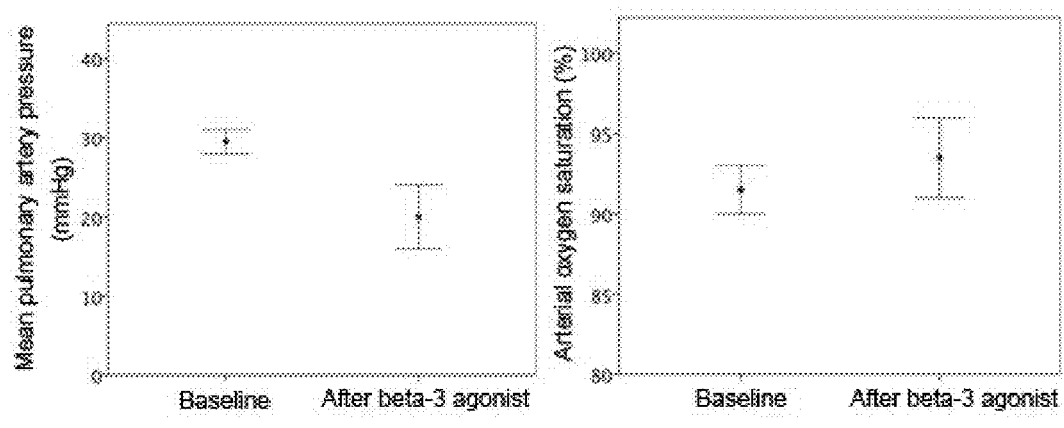
FIG. 3 shows the effect of the administration of BRL 37344 on mean PAP and arterial oxygen saturation (mean±standard error) in chronic pre-capillary PH.

Similarly, in the pre-capillary chronic PH model, administration of the selective β3 adrenergic agonist BRL 37344 was associated with a 32% decrease of the mean PAP (29.5±2.1 to 20.0±5.7 mmHg), a 25% reduction of systolic PAP (37.5±6.4 to 28.0±8.5 mmHg) and a 2% increase of oxygen saturation, without significant changes in systemic blood pressure and in heart rate (FIG. 3).

3. Effect of Chronic Endovenous Treatment with BRL37344 in Post-Capillary Chronic PH: Blind, Randomized Experimental Study.

Chronic PH was generated in 8 pigs by means of surgical stenosis of the lower pulmonary venous confluence as described above. The animals were randomized into BRL37344 (10 μg/Kg/day) vs. physiological saline for 14 days, administered by means of ALZET® osmotic pumps coupled to a catheter inserted in the jugular vein. Right heart catheterization was performed pre- and post-treatment.

The baseline characteristics of animals after pulmonary embolization did not differ between the groups randomized into β3 agonist BRL37344 or placebo (Table 2).

TABLE 2

Baseline characteristics of animals with chronic PH randomized into chronic treatment with BRL37344 or physiological saline by means of osmotic pumps.

|  | Control group (N = 4) | Group with BRL37344 (N = 4) | P |
|---|---|---|---|
| Weight (Kg) | 46.1 ± 9.8 | 48.5 ± 10.3 | 0.75 |
| $O_2$ saturation (%) | 95.0 ± 1.2 | 89.0 ± 6.3 | 0.16 |
| Heart rate (bpm) | 73.5 ± 9.6 | 75.8 ± 4.6 | 0.69 |
| Mean blood pressure (mmHg) | 90.5 ± 10.9 | 93.0 ± 9.1 | 0.74 |
| Mean pulmonary artery pressure (mmHg) | 34.3 ± 7.9 | 33.7 ± 3.6 | 0.90 |
| Cardiac output (L/min) | 5.4 ± 1.3 | 5.7 ± 0.9 | 0.73 |
| Pulmonary vascular resistances (WU) | 4.6 ± 4.1 | 4.8 ± 1.2 | 0.93 |
| RV end-diastolic volume (ml/m$^2$) | 95.1 ± 19.7 | 108.7 ± 7.4 | 0.25 |
| RV end-systolic volume (ml/m$^2$) | 37.9 ± 17.7 | 47.4 ± 7.9 | 0.37 |
| RV ejection fraction (%) | 61.4 ± 9.9 | 56.5 ± 5.0 | 0.42 |
| RV mass (g/m$^2$) | 28.6 ± 10.8 | 27.0 ± 3.3 | 0.80 |

Figure 4:
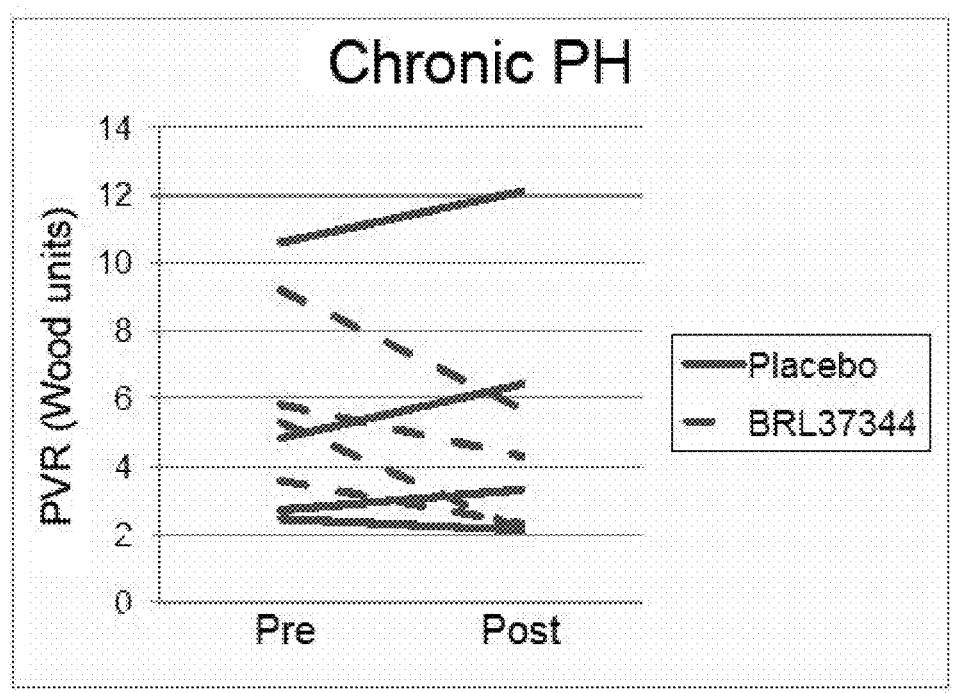
FIG. 4 shows changes 14 days after starting treatment with respect to the initial condition (placebo represented by a solid line and BRL37344 by a discontinuous line) of PVR in 8 animals with post-capillary chronic PH.

After 14 days, chronic therapy with the β3 agonist BRL37344 produced a significant reduction of pulmonary vascular resistances (PVRs) compared with placebo (−1.2±1.6 vs. +1.3±1.2 WU, p=0.042, FIG. 4). No significant differences were observed in the change in systemic mean blood pressure (2.3±6.9 vs. 4.3±7.0 mmHg, p=0.25) or in heart rate (−8.2±15.1 vs. 3.0±28.2 bpm; p=0.49) between the group treated with the β3 agonist and placebo.

4. Effect of Chronic Oral Treatment with Mirabegron in Post-Capillary Chronic PH: Blind, Randomized Experimental Study.

Figure 5:
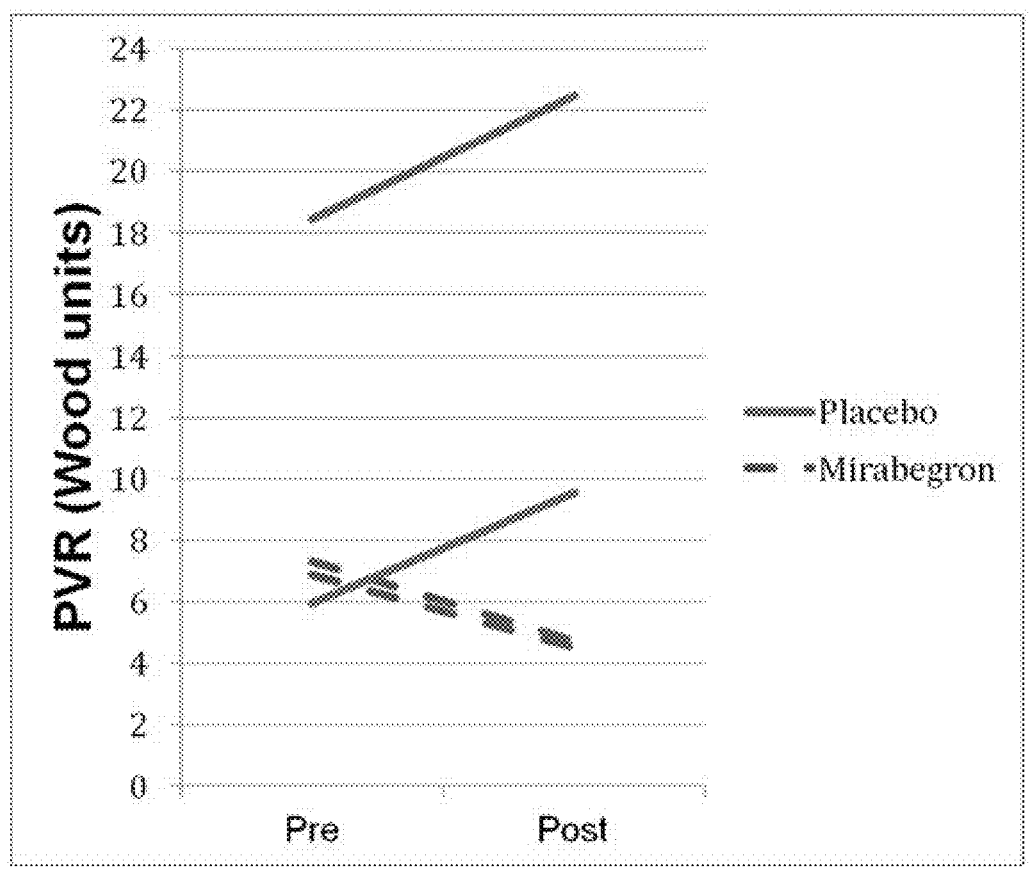
FIG. 5 shows changes 14 days after starting treatment with respect to the initial condition (placebo represented by a solid line and Mirabegron by a discontinuous line) of PVR in 8 animals with post-capillary chronic PH.

Another cohort of animals with post-capillary chronic PH were randomized into chronic therapy for 14 days with Mirabegron (Myrbetrig® 50 mg/12 hours) or placebo. Right heart catheterization was performed pre- and post-treatment. In an intermediate analysis (N=4), a reduction of PVRs was observed after 14 days in the group treated with the β3 agonist compared with an increase of PVRs in the control group (FIG. 5).

5. Immunofluorescence of the Human Pulmonary Artery

Samples of main pulmonary artery were obtained from a heart transplant recipient and donor. Two primary antibodies specific for β3 receptors (CAPG and MAPW) were used. DAPI, which stains the nuclei blue, and secondary antibody AF647, which recognizes the primary antibody and stains it red, were used as fluorophores. A Zeiss LSM700 confocal microscope was used.

Figure 6:
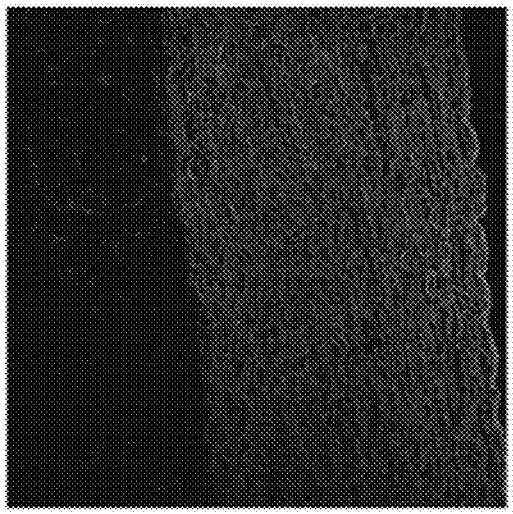
FIG. 6 shows the immunofluorescence of β3 receptors in a human pulmonary artery.
Figure 6:
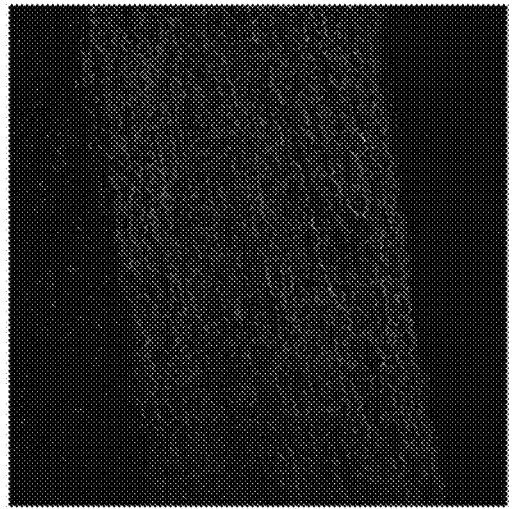

The presence of β3 adrenergic receptors in the tunica media and endothelium was seen in the main PA of the donor and of the recipient. The results were replicated with 2 anti-β3 specific antibodies (FIG. 6).

Discussion

In a broad spectrum of chronic PH, the treatment with β3 agonists produced a significant reduction of PAP and of pulmonary vascular resistances. These effects were observed without finding significant changes in systemic blood pressure or in heart rate, which suggests that the possible side effects detrimental to systemic circulation are very low (compared to other vasodilators used in this disease).

It was also observed that in a situation of a sudden increase of pulmonary pressure, the administration of BRL 37344 produces a very important acute reduction of PAP, which suggests that selective β3 agonists can be of use in the acute pulmonary thromboembolism scenario, a vital emergency for which there are very few therapeutic alternatives.

It can therefore be concluded that the administration of selective beta-3 adrenergic agonists represents an effective treatment for both acute and chronic PH of a different etiology.

The invention claimed is:

1. A method for treating pulmonary hypertension due to left heart disease (group 2 PH) in a subject in need thereof, the method comprising administering to said subject an effective amount of a selective beta-3 adrenergic receptor agonist compound or a pharmaceutically acceptable salt thereof, wherein said selective beta-3-adrenergic receptor agonist compound is selected from the group consisting of YM178 (Mirabegron) and BRL 37344, such that said group 2 PH in said subject is treated.

2. The method of claim 1, wherein the pulmonary hypertension comprises acute pulmonary thromboembolism.

3. A method of treating pulmonary hypertension due to left heart disease (group 2 PH) in a subject in need thereof, the method comprising administering to said subject an effective amount of YM178 (Mirabegron) or a pharmaceutically acceptable salt thereof, such that said group 2 PH in said subject is treated.

4. The method of claim 1, wherein said selective beta-3-adrenergic receptor agonist compound is YM178 (Mirabegron).

5. The method of claim 1, wherein said selective beta-3-adrenergic receptor agonist compound is BRL 37344.

6. The method of claim 1, wherein the subject is a human.

7. The method of claim 1, wherein the subject does not experience significant side effects on systemic circulation.

8. The method of claim 7, wherein the subject does not experience significant changes in systemic blood pressure.

9. The method of claim 7, wherein the subject does not experience significant changes in heart rate.

* * * * *